United States Patent [19]

Bastart et al.

[11] Patent Number: 5,670,658
[45] Date of Patent: Sep. 23, 1997

[54] PROCESS FOR PREPARING 7-TRIALKYLSILYL BACCATIN III

[75] Inventors: Jean-Pierre Bastart, Lesigny; Jean-Pierre Leconte, Brunoy, both of France

[73] Assignee: Rhone-Poulenc Rorer S.A., Antony, France

[21] Appl. No.: 722,103

[22] PCT Filed: Apr. 3, 1995

[86] PCT No.: PCT/FR95/00419

§ 371 Date: Oct. 3, 1996

§ 102(e) Date: Oct. 3, 1996

[87] PCT Pub. No.: WO95/26967

PCT Pub. Date: Oct. 12, 1995

[30] Foreign Application Priority Data

Apr. 5, 1994 [FR] France .................. 94 03979

[51] Int. Cl.⁶ .................................. C07D 305/14
[52] U.S. Cl. ........................................ 549/214
[58] Field of Search ............................. 549/214

[56] References Cited

U.S. PATENT DOCUMENTS

| | | | |
|---|---|---|---|
| 5,405,972 | 4/1995 | Holton et al. | 549/214 |
| 5,449,790 | 9/1995 | Zheng et al. | 549/214 |
| 5,597,931 | 1/1997 | Danishefsky et al. | 549/214 |
| 5,599,820 | 2/1997 | Ojima et al. | 549/214 X |

FOREIGN PATENT DOCUMENTS 366840  10/1989  European Pat. Off. .

OTHER PUBLICATIONS

Denis et al., J. Am. Chem. Soc., vol. 110 (17), pp. 5917–5919, Jun. 1988.

*Primary Examiner*—Paul F. Shaver
*Attorney, Agent, or Firm*—Finnegan, Henderson, Farabow, Garrett & Dunner, L.L.P.

[57] ABSTRACT

The present invention relates to a novel process for the preparation of 7-trialkylsilylbaccatin III of general formula:

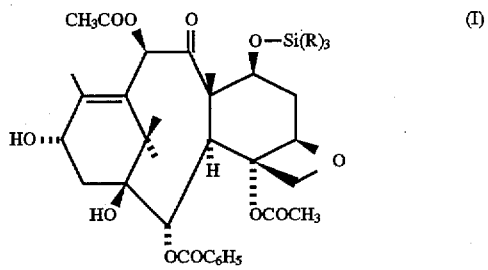

in which the symbols R, which may be identical or different, represent alkyl radicals containing 1 to 4 carbon atoms which are optionally substituted with a phenyl radical, starting with 10-deacetylbaccatin III of formula:

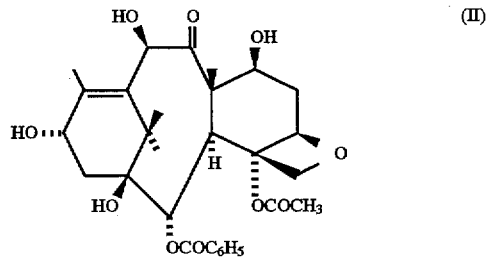

In the general formula (I), each of the symbols R preferably represents a straight or branched alkyl radical containing 1 to 4 carbon atoms. Even more particularly, each of the symbols R represents an ethyl radical.

10 Claims, No Drawings

PROCESS FOR PREPARING 7-TRIALKYLSILYL BACCATIN III

It is known, in particular according to J-N. Denis and A. E. Greene, J. Amer. Chem. Soc., 110, 5917–5919 (1998), to prepare a product of general formula (I) from 10-deacetylbaccatin III of formula (II) by first carrying out the selective silylation at position −7 of the taxane ring system in order to obtain 7-trialkylsilyl-10-deacetylbaccatin III, and then by selectively acetylating at position −10 the 7-trialkylsilyl-10-deacetylbaccatin III thus obtained.

According to the known process, the silylation reaction is carried out by treating 10-deacetylbaccatin III with excess trialkylsilyl halide of general formula:

in which Hal represents a halogen atom and R is defined as above, working in a basic organic solvent such as pyridine, at a temperature in the region of 20° C. Generally, 7-trialkylsilyl-10-deacetylbaccatine III is obtained with a yield in the region of 85%.

According to the known process, the acetylation is carried out by treating 7-triethylsilyl-10-deacetylbaccatin III with excess acetyl chloride, working in a basic organic solvent such as pyridine, at a temperature in the region of 0° C. Generally, 7-trialkylsilyloxybaccatin III of formula (I) is obtained with a yield of 85% from 7-triethylsilylbaccatin III.

Thus, according to the known process, a 7-trialkylsilylbaccatin III is obtained with a yield in the region of 72%.

It has now been found, and this forms the subject of the present invention, that the product of general formula (I) may be obtained with better yields by carrying out the silylation and the acetylation without isolation of the intermediate 7-trialkylsilyl-10-deacetylbaccatin III.

According to the invention, 10-deacetylbaccatin III, dissolved in a basic organic solvent chosen from pyridine and pyridines substituted with one or more alkyl radicals containing 1 to 4 carbon atoms, is treated with a silylating agent of general formula (III) at a temperature between 0° and 15° C., and then with acetic anhydride at a temperature in the region of 20° C.

The use of the process according to the invention requires the use of a much smaller excess of silylating agent than in the known process. Generally, from 1.5 to 2.5 mol of silylating agent are used per mole of 10-deacetylbaccatin III used.

Generally, 5 to 7 mol of acetic anhydride are used per mole of 10-deacetylbaccatin III used.

The 7-trialkylsilylbaccatin III may be isolated after precipitation in water and crystallization, from its solution in an aliphatic ester such as ethyl acetate, using an ether such as isopropyl ether. Generally, the yield is in the region of 80% from the 10-deacetylbaccatin III used.

The 7-trialkylsilylbaccatin III, obtained according to the process of the present invention, may be used, after isolation or dissolved in an aliphatic ester such as ethyl acetate, in order to prepare paclitaxel or derivatives thereof according to known processes as described, for example, in European Patent EP-0,336,840 or in International Application WO 92/09589.

The example which follows illustrates the use of the process according to the invention.

EXAMPLE

To a solution of 293.9 g of 10-deacetylbaccatin III in 2.7 liters of pyridine are added, over 1 hour 20 minutes, 182 g of triethylsilyl chloride. The solution obtained is stirred for 40 hours at 5° C. 360 g of acetic anhydride are then added while maintaining the temperature at 5° C. The suspension obtained is stirred for 48 hours at 20° C. and is then poured onto 40 liters of ice-cold water. The precipitate obtained is separated by filtration and then washed with 8 times 2 liters of water and finally dissolved in 3 liters of ethyl acetate. The organic phase is dried over magnesium sulphate. After filtration and concentration under reduced pressure, the product obtained is crystallized from isopropyl ether. 7-triethylsilylbaccatin III is thus obtained with a yield of 77%, the characteristics of which product are as follows:

melting point: 254° C.

proton nuclear magnetic resonance spectrum:(400 MHz; $CDCl_3$, δ in ppm):0.58 (mt, $6H:CH_2$ ethyl); 0.92 (t, J=7.5 Hz, $9H:CH_3$ ethyl); 1.02 (s, $3H:CH_3$); 1.18 (s, $3H:CH_3$); 1.68 (s, $3H:CH_3$); 1.75 (broad s, 1H:OH at 1); 1.87 and 2.53 (2 mt, 1H each:$CH_2$ at 6); 2.18 (s, $6H:CH_3$ and $COCH_3$); 2.27 (mt, $2H:CH_2$ at 14); 2.28 (s, $3H:COCH_3$); 2.47 (broad s, 1H:OH at 13); 3.88 (d, J=7 Hz, 1H:H3); 4.13 and 4.30 (2d, J=8.5 Hz, 1H each:$CH_2$ at 20); 4.50 (dd, J=11 and 7 Hz, 1H:H at 7); 4.81 (mt, 1H:H at 13); 4.95 (broad d, J=10 Hz, 1H:H at 5); 5.63 (d, J=7 Hz, 1H:H2); 6.46 (s, 1H:H at 10); 7.46 (t, J=8.5 Hz, 2H:—$OCOC_6H_5$ meta H); 7.60 (t, J=8.5 Hz, 1H:—$OCOC_6H_5$ para H); 8.10 (d, J=8.5 Hz, 2H:—$OCOC_6H_5$ ortho H).

We claim:

1. Process for the preparation of 7-trialkylsilylbaccatin III of general formula:

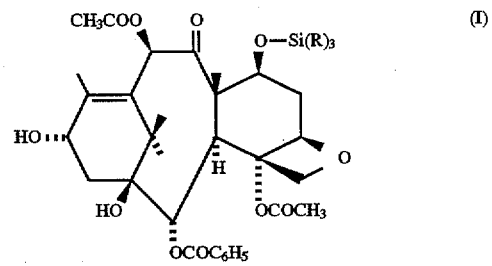

in which the symbols R, which may be identical or different, represent straight or branched alkyl radicals containing 1 to 4 carbon atoms which are optionally substituted with a phenyl radical, characterized in that 10-deacetylbaccatin III of formula:

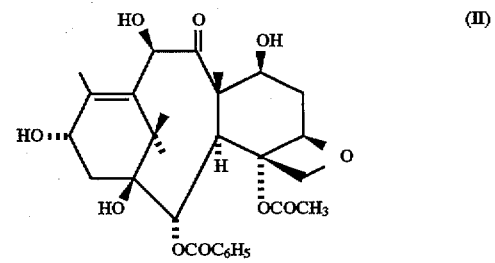

is treated with a silylating agent of general formula:

in which R is defined as above, then with acetic anhydride without isolating the intermediate 7-trialkylsilyl-10-deacetylbaccatin III.

2. Process according to claim 1, characterized in that the process is performed in a basic organic solvent.

3. Process according to claim 2, characterized in that the basic organic solvent is chosen from pyridine and pyridines substituted with one or more alkyl radials containing 1 to 4 carbon atoms.

4. Process according to claim 2, characterized in that the basic organic solvent is pyridine.

5. Process according to either of claims 1 and 2, characterized in that from 1.5 to 2.5 mol of silylating agent are used per mol of 10-deacetylbaccatin III used.

6. Process according to either of claims 1 and 2, characterized in that from 5 to 7 mol of acetic anhydride are used per mole of 10-deacetylbaccatin III used.

7. Process according to either of claims 1 and 2, characterized in that the treatment with the silylating agent is carried out at a temperature between 0° and 15° C.

8. Process according to either of claims 1 and 2, characterized in that the treatment with acetic anhydride is carried out at a temperature in the region of 20° C.

9. Process according to one of claims 1 to 8 for the preparation of a 7-trialkylsilylbaccatin III of general formula (I) in which each of the symbols R represents an alkyl radical containing 1 to 3 carbon atoms.

10. Process according to one of claims 1 to 8 for the preparation of a 7-trialkylsilylbaccatin III of general formula (I) in which each of the symbols R represents an ethyl radical.

* * * * *